(12) United States Patent
Pearl (10) Patent No.: US 6,589,282 B2
(45) Date of Patent: Jul. 8, 2003

(54) MODULAR SHOULDER PROSTHESES

(75) Inventor: Michael L. Pearl, Los Angeles, CA (US)

(73) Assignee: Implex Corporation, Allendale, NJ (US)

( * ) Notice: Subject to any disclaimer, the term of this patent is extended or adjusted under 35 U.S.C. 154(b) by 0 days.

(21) Appl. No.: 09/752,701

(22) Filed: Dec. 29, 2000

(65) Prior Publication Data

US 2001/0041940 A1 Nov. 15, 2001

Related U.S. Application Data

(60) Provisional application No. 60/174,139, filed on Dec. 31, 1999.

(51) Int. Cl.[7] .................................................. A61F 2/40
(52) U.S. Cl. ................................. 623/19.14; 623/19.11; 623/23.11
(58) Field of Search ........................... 623/19.14, 19.11, 623/19.12, 19.13, 22.11, 22.44, 22.45, 23.11

(56) References Cited

U.S. PATENT DOCUMENTS

| | | | |
|---|---|---|---|
| 4,865,605 A | | 9/1989 | Dines et al. |
| 4,919,670 A | | 4/1990 | Dale et al. |
| 5,002,581 A | * | 3/1991 | Paxson et al. |
| 5,282,865 A | | 2/1994 | Dong |
| 5,314,479 A | * | 5/1994 | Rockwood, Jr. et al. |
| 5,358,526 A | * | 10/1994 | Tornier |
| 5,489,309 A | | 2/1996 | Lackey et al. |
| 5,549,682 A | | 8/1996 | Roy |
| 5,702,486 A | * | 12/1997 | Craig et al. |
| 5,910,171 A | | 6/1999 | Kummer et al. |
| 5,961,555 A | | 10/1999 | Huebner |
| 6,033,439 A | | 3/2000 | Camino et al. |
| 6,045,582 A | * | 4/2000 | Prybyla |
| 6,102,953 A | | 8/2000 | Huebner |
| 6,120,542 A | | 9/2000 | Camino et al. |
| 6,129,764 A | | 10/2000 | Servidio |

FOREIGN PATENT DOCUMENTS

| | | |
|---|---|---|
| WO | 98/46172 | 10/1998 |
| WO | 00/15154 | 3/2000 |

OTHER PUBLICATIONS

Equinoxe, *Technique Operatoire*; Shoulder Arthroplasty Conference, Paris, France; Jan. 24, 2000.

* cited by examiner

*Primary Examiner*—Pedro Philogene
(74) *Attorney, Agent, or Firm*—Duane Morris LLP (57) ABSTRACT

A humeral prosthetic device having a body, a stem for anchoring the device in a humeral canal of a humerus, and a head for replacing a natural humeral head of the humerus. The head is disposed at a selected angle relative to the stem and at least one of the body and stem may control the selected angle of the head relative to the stem. Further, the stem may include an extension for coupling the stem to the body. The extension may be disposed on an axis parallel to and offset from a center line of the stem for providing a lateral offset of the body relative to the stem upon reversal of the stem in the humeral canal. The humeral prosthetic device may further include an insert which coacts with the body and the head of the device to provide superior, inferior, anterior, and posterior positioning of the head relative to the body.

20 Claims, 8 Drawing Sheets

MODULAR SHOULDER PROSTHESES

RELATED APPLICATIONS

This application claims the benefit of Provisional application No. 60/174,139 filed Dec. 31, 1999.

FIELD OF THE INVENTION

This invention relates to bone prostheses and more particularly to a modular shoulder prosthetic device that comprises a head, a body, and a stem.

BACKGROUND OF THE INVENTION

The design of humeral prostheses for replacement of the shoulder joint has evolved through the years in at least three different stages. First stage designs were relatively simple, usually consisting of a partial ball on a stem as exemplified in U.S. Pat. No. 3,694,820 issued to Scales et al., assigned to the National Research Development Corporation of London, England. Stage two designs were more complex due to their modular nature, which typically consisted of a more sophisticated stem structure that was interchangeable in size and joined to a separate head of a selected size. A typical stage two humeral prosthesis is described in U.S. Pat. No. 5,507,817 issued to Craig et al., assigned to the Kirschner Medical Corporation. Third stage designs, which are most recent and represent the state of the art, typically consist of a three component modular structure including a head, body, and stem. These designs provide a change in the inclination of the head with resection angles of 35 to 50 degrees from the axis of the stem and variable offset of the head relative to the body. An example of a third stage humeral prosthesis design is described in U.S. Pat. No. 5,358,526 issued to Alain Tonier, assigned to Etablissements Tonier of Saint-Ismier, France.

Several commonly used humeral prosthesis designs have been studied and the findings reported in a paper entitled, GEOMETRIC ANALYSIS OF COMMONLY USED PROSTHETIC SYSTEMS FOR PROXIMAL HUMERAL REPLACEMENT, by M. L. Pearl, M.D. and Sam Kurutz, BS, published in the *Journal of Bone and Joint Surgery*, May 1999@660. The findings of this study tended to show that, despite their increasing sophistication, the second stage humeral prosthesis designs did not replicate normal anatomy, thus, precluding restoration of the normal biomechanics of the glenohumeral joint.

The above study, and other biomechanical studies offer several reasons to expect deranged biomechanics after humeral replacement. These reasons include: superior and lateral shifting of the center of rotation of the glenohumeral joint by 15 or more millimeters from the original position after humeral replacement; a diminished arc of the articulated surface as compared with the anatomical joint; patient to patient variations for which there is insufficient accommodation in most prostheses; variations in the location of the axis of the humeral canal as reamed; and common surgical techniques for removing the anatomical humeral head limit the positioning of the prosthetic head because they remove the anatomical humeral head at a standard or predetermined angle prior to definition of the prosthetic stem canal position.

Hence, a humeral prosthesis is needed which substantially allows replication of the normal anatomy.

SUMMARY OF THE INVENTION

According to an aspect of the present invention, a humeral prosthetic device comprises a body; a stem for anchoring the device in a humeral canal of a humerus, the stem coupled to a first area of the body; and a head for replacing a natural humeral head of the humerus, the head coupled to a second area of the body and disposed at a selected angle relative to the stem. At least one of the body and stem controls the selected angle of the head relative to the stem.

According to another aspect of the present invention, a humeral prosthetic device comprises a body; a stem for anchoring the device in a humeral canal of a humerus, the stem coupled to a first area of the body and defining a center line for centering the stem in the humeral canal; and a head for replacing a natural humeral head of the humerus, the head coupled to a second area of the body and disposed at a selected angle relative to the stem; the stem including an extension for coupling the stem to the body, the extension disposed on an axis parallel to and offset from the center line for providing a lateral offset of the body relative to the stem upon reversal of the stem in the humeral canal.

According to a further aspect of the present invention, a humeral prosthetic device comprises an insert which coacts with a body and a head of the device to provide superior, inferior, anterior, and posterior positioning of the head relative to the body.

BRIEF DESCRIPTION OF THE DRAWINGS

The advantages, nature, and various additional features of the invention will appear more fully upon consideration of the illustrative embodiments now to be described in detail in connection with accompanying drawings wherein:

FIGS. 6A and 6B illustrate how changing the stem/body offset can better accommodate certain anatomical central axes, wherein FIG. 6A illustrates metaphyseal impingement with a prior art body offset position that is avoided by a lateral offset position as illustrated in FIG. 6B that is achieved with a stem reversal;

It should be understood that the drawings are for purposes of illustrating the concepts of the invention and are not necessarily to scale.

DETAILED DESCRIPTION OF THE INVENTION

Figures 1A, 1B:
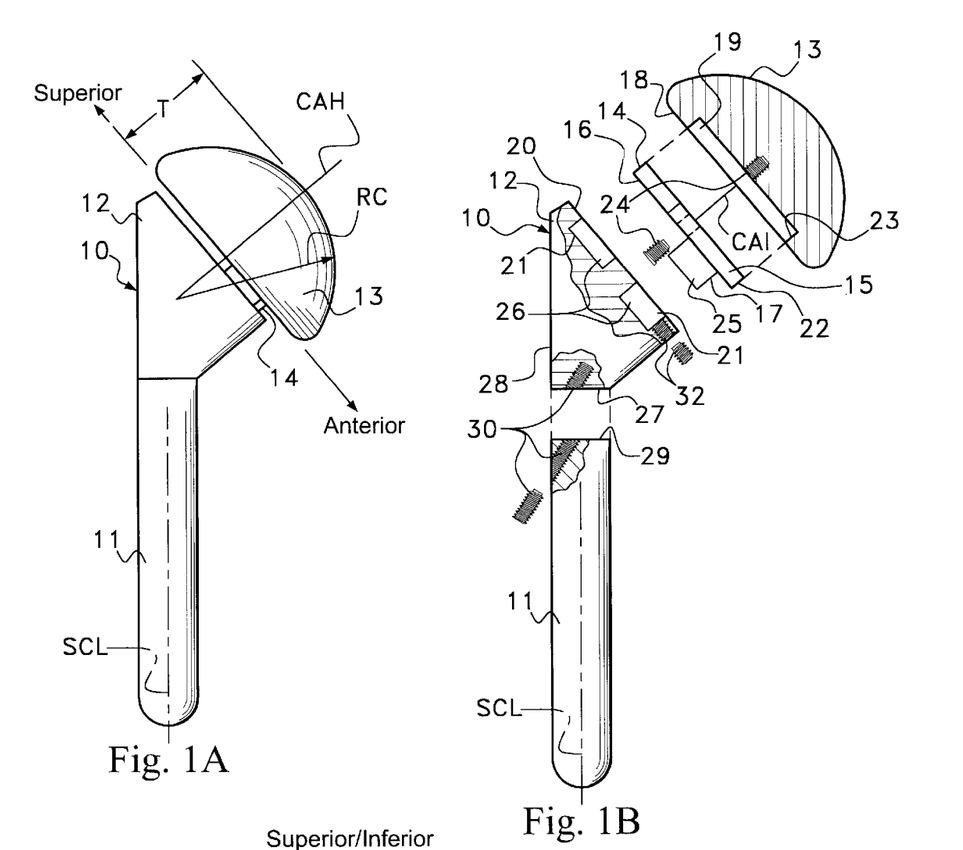
FIG. 1A is a side elevational view of a modular humeral prosthetic device made in accordance with a first exemplary embodiment of the present invention.
FIG. 1B is an exploded side elevational view of the prosthetic device of FIG. 1A with the head, body, and stem shown in partial section.
Figure 1C:
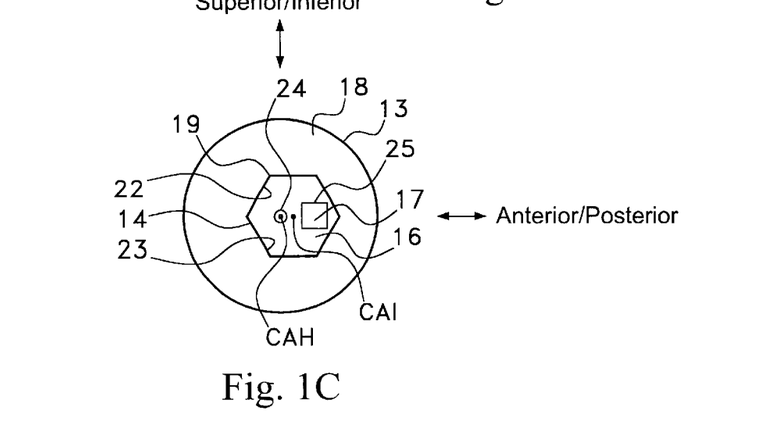
FIG. 1C is an underside plan view of the head of the prosthetic device of FIGS. 1A and 1B.
Figure 2A:
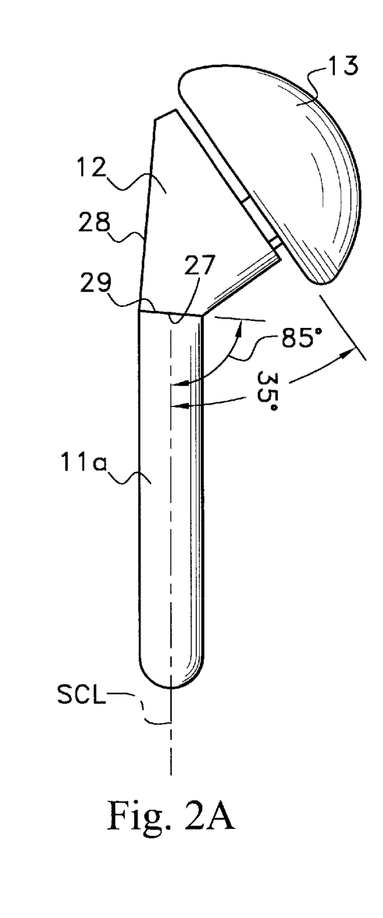
FIGS. 2A–2D are side elevational views of the prosthetic device of FIGS. 1A–1C, which illustrate a few possible stem/body combinations wherein the stem is configured to enable the head-to-stem angle and lateral body offset to be selected.
Figure 2B:
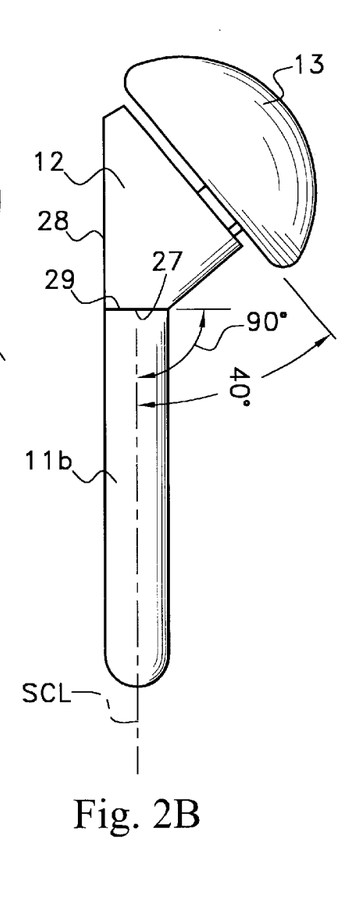
Figure 2C:
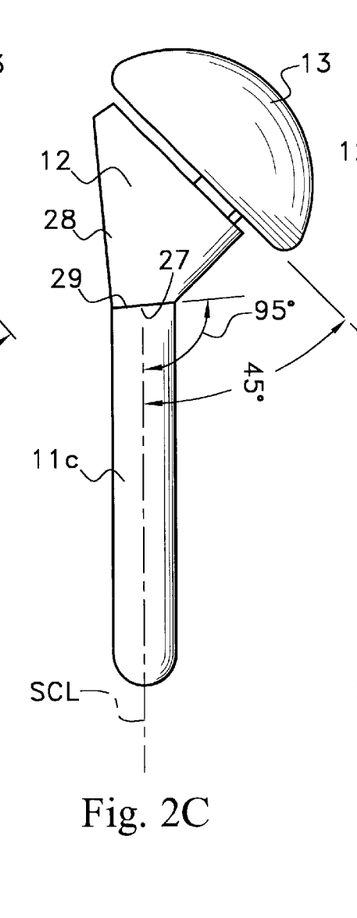
Figure 2D:
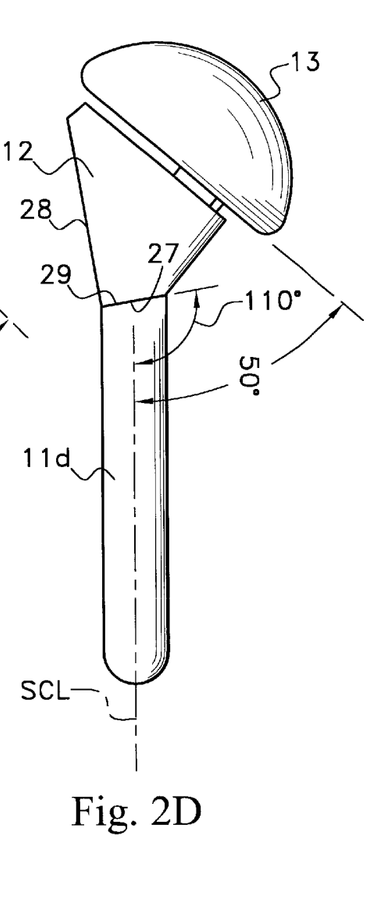
Figure 3A:
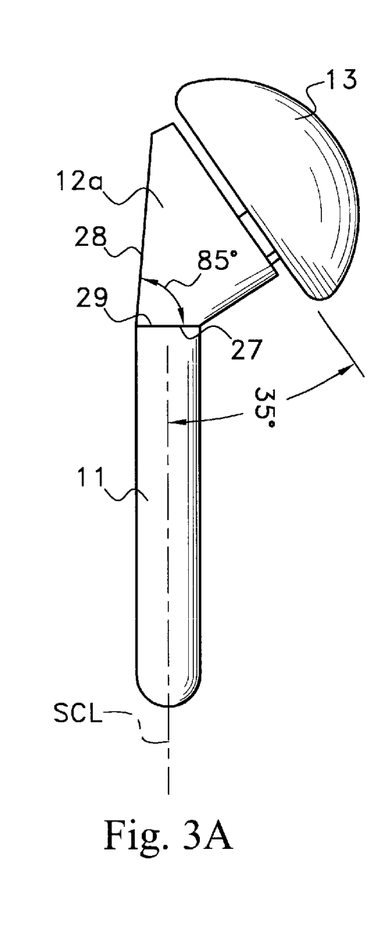
FIGS. 3A–3D are side elevational views of the prosthetic device of FIGS. 1A–1C, which illustrate a few possible stem/body combinations wherein the body is configured to enable the head-to-stem angle and lateral body offset to be selected.
Figure 3B:
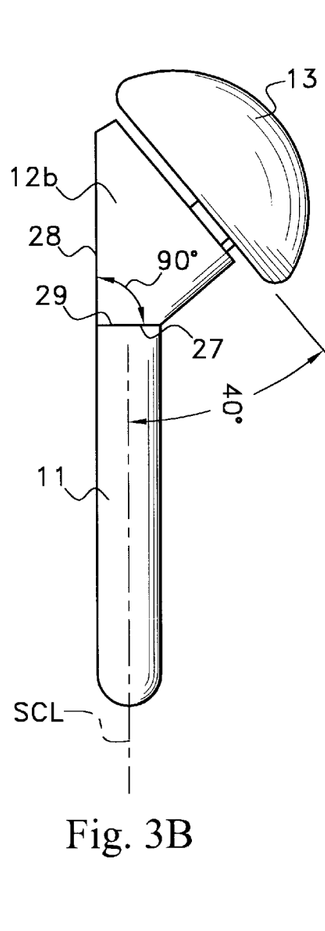
Figure 3C:
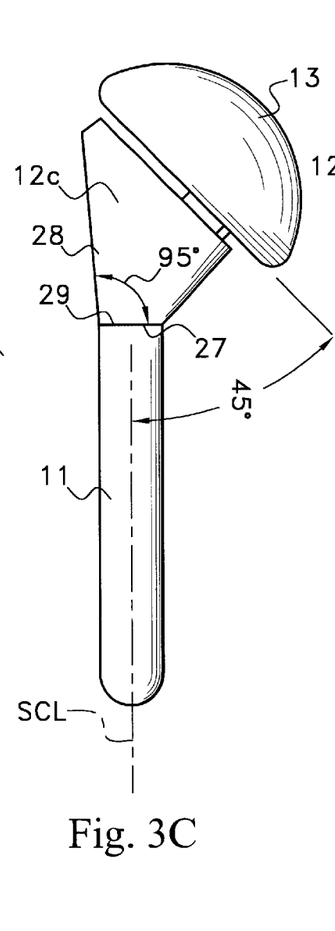
Figure 3D:
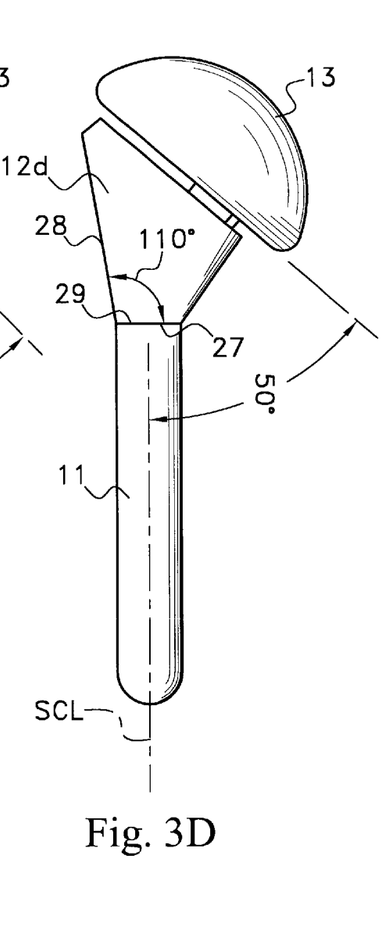

Referring to the drawings wherein like reference numerals identify similar or like elements throughout the several views and initially to FIGS. 1A–1C, a modular humeral prosthetic device 10 is illustrated in accordance with a first exemplary embodiment of the present invention. As illustrated, the prosthetic device comprises three separate modules: a stem 11; a body 12; and a head 13.

The stem 11 or body 12 of the prosthetic device 10 may be configured in a manner which enables a plurality of head-to-stem angles and lateral (metaphyseal) offsets of the body 12 to be selected. FIGS. 2A–2D illustrate how the stem 11 may be configured to enable the head-to-stem angle and lateral body offset to be selected. As illustrated in each of FIGS. 2A–2D, the angle of the stem's superior end wall 29, relative to the stem's center line SCL, is varied by providing a series of stems 11a through 11d with incrementally different superior end wall angles. The stems 11a–11d are combined with bodies 12, which have the same construction in each of the figures, i.e., with a base wall 27 to rear wall 28 angle of about 90°. In the examples depicted in the figures, the angle of the superior end wall 29 may range from an acute angle of 85° in FIG. 2A, which may provide a head-to-stem angle of 35°, to an obtuse angle of 110° in FIG. 2D, which may provide a head-to-stem angle of 110°. The selected stem 11a–11d may be secured to the body 12 using any conventional fixation system, such as a simple set screw and screw aperture arrangement 30 shown in FIG. 1B.

FIGS. 3A–3D illustrate how the body 12 may be configured to enable the head-to-stem angle and lateral body offset to be selected. As illustrated in each of FIGS. 3A–3D, a series of bodies 12a–12d are provided with incrementally different body base wall 27 to the body rear wall 28 angles. The bodies 12a–12d are combined with stems 11 which have the same construction in each of the figures, i.e., with a superior end wall 29 to the stem center line SCL angle of about 90°. The stems 11 are typically secured to the bodies 12a–12d using any conventional fixation system, such as a simple set screw and screw aperture arrangement 30 shown in FIG. 1B.

Figure 10A:
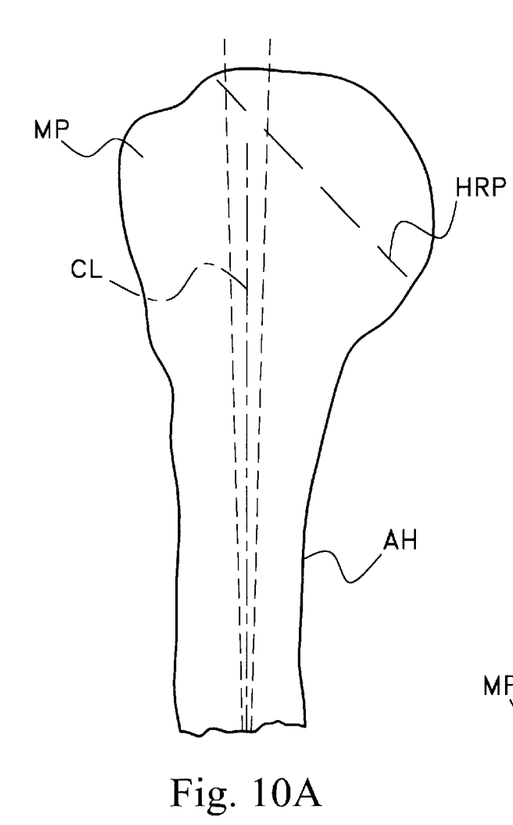
FIG. 10A is a side elevational view of exemplary humerus from a cadaveric study illustrating the potential range of orthopedic axes and a typical head resection plane.
Figure 10B:
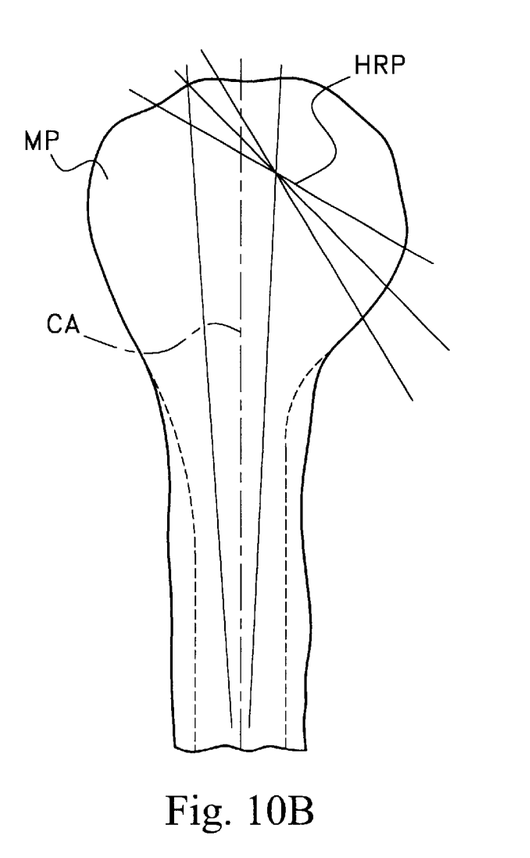
FIG. 10B is a modification of FIG. 10A illustrating how the plane of the head resection may vary with surgical technique adding to the potential variability of the head, body, stem relationship even after the orthopedic axis is defined.

The importance of selectable lateral body offset, as provided by the prosthetic device of the present invention, is better understood with reference to FIGS. 10A and 10B which respectively illustrate the potential range of orthopedic axes and a typical head resection plane and how the plane of the head resection may vary with surgical technique adding to the potential variability of the head, body, stem relationship even after the orthopedic axis is defined. In FIG. 10A, a sample anatomical humerus AH is depicted which has a sufficient cross-section to allow the humeral canal to have a range of angles departing from the center line CL both in the medial/lateral and anterior/posterior directions. This degree of freedom is typically not recognized in existing descriptions of surgical techniques utilized by the surgeon performing a humeral prosthetic replacement. The typical resection plane is identified as HRP. FIG. 10B depicts the full range of canal axes plus head resection planes which illustrate that, once defined by the surgeon intraoperatively, the orthopedic axis (canal center) may be accompanied by a choice of head resection planes.

It should be clearly evident by comparing FIGS. 2A–2D and comparing FIGS. 3A–3D, that as the head-to-stem inclination angle changes, the metaphyseal offset of the body 12 changes.

The metaphyseal region is where the greatest amount of in-growth of native bone into the prosthesis occurs, therefore, the size and shape of this portion of the prosthesis is more important than as heretofore been recognized, in particular with respect to accommodating the native anatomy.

Press fit (non-cemented) applications of the first stage and second stage prosthetic systems discussed earlier, require optimal fit and fill in this region. Furthermore, extreme mismatches of body/stem shapes simply will not fit in the bone. Until now, the variability of metaphyseal shape of the anatomical humerus has been the least studied. It is clear that the metaphyseal offset from the stem canal must be just as important as head offset. After all, the head position relative to the stem is determined by the shape of the metaphyseal region of the bone.

If appropriate consideration is given to metaphyseal offset, it is in this region that optimal fit and fill may be achieved to promote stability and in-growth of the prosthesis. The prosthetic device of the present invention provides metaphyseal offset selectivity which enables a surgeon to take better advantage of anatomic variability in this area and variations inherent in surgical techniques. Translating this into practical terms, the surgeon is better able to position the prosthesis of the present invention in the center of the metaphysis and still effectively replicate the anatomic position of the patient's articular surface.

Referring again to FIGS. 1A–1C, the head 13 is typically made available in a multiplicity of sizes, based on radius of curvature and thickness, to replace different size anatomical humeral head surfaces. The head 13 is positioned relative to the body 12 and locked thereto via an insert 14. The insert 14 comprises a generally disc-shape member 15 and a locking projection 17 depending from a lower surface 16 of the member 15, laterally offset from a central axis CAI thereof. The disc-shape member 15 of the insert 14 nests in a recess 19 in a backside 18 of the head 13, the recess 19 being laterally offset from a central axis CAH of the head. The locking projection 17 is received in one of two or more apertures 21 defined in an inclined wall 20 of the body 12. Peripheral surfaces 22, 23 of the disc-shape member 15 and the head recess 19 are configured to enable the insert 14 to be rotatively positioned relative to the head 13 in a selective manner. A set screw and screw aperture arrangement 24 or other suitable arrangements, e.g. tapered press-fits, may used to retain the insert in the recess 19 of the head 13. Peripheral surfaces 25, 26 of the insert locking projection 17 and the body apertures 21 are configured to enable the insert 14/head 13 to be rotatively positioned relative to the body 12 in a selective manner. A set screw and screw aperture arrangement 32 may be used to retain the insert locking projection 17 in the selected body aperture 21 or other suitable arrangements, e.g. tapered press-fits, may used to retain the insert locking projection 17 in the aperture 21 of the body 12.

Because the recess 19 in the backside 18 of the head 13 is laterally offset from the central axis CAH of the head 13, the offset of the insert locking projection 17 relative to the central axis CAH of the head 13 can be varied by incrementally by rotating the insert 14 relative to the head 13. Incremental rotation of the insert 14 relative to the head 13 may be accomplished by forming the peripheral surfaces 22, 23 of the disc-shape member 15 and head recess 19 in a hexagonal configuration, which permits the insert 14 to be placed in one of six rotational positions in the head 13. Other head/recess peripheral surface arrangements, e.g., octagonal, cylindrical, splined peripheral surfaces, may be used to increase the number of rotational positions available for placing the insert 14 in the head 13. Incremental rotation of the insert 14 relative to the body 12 may be accomplished by forming the peripheral surfaces 25, 26 of the insert locking projection 17 and the body apertures 21 in a square configuration, which permits the insert 14 (and the head 13 attached thereto) to be located in one of four offset positions relative to the body 12. Other locking projection/aperture peripheral surface arrangements, e.g., octagonal, cylindrical, splined peripheral surfaces, may be used to increase the number of positions available for locating the insert 14 relative to the body 12.

The above described insert/head/body features permit very precise superior, inferior, anterior, and posterior positioning of the head 13 relative to the body 12 and stem 11. A plurality of inserts 14 with various locking projection offsets can be provided to make superior, inferior, anterior, and posterior, positioning of the head 13 relative to the body 12 and stem 11 virtually limitless.

Figures 4, 5:
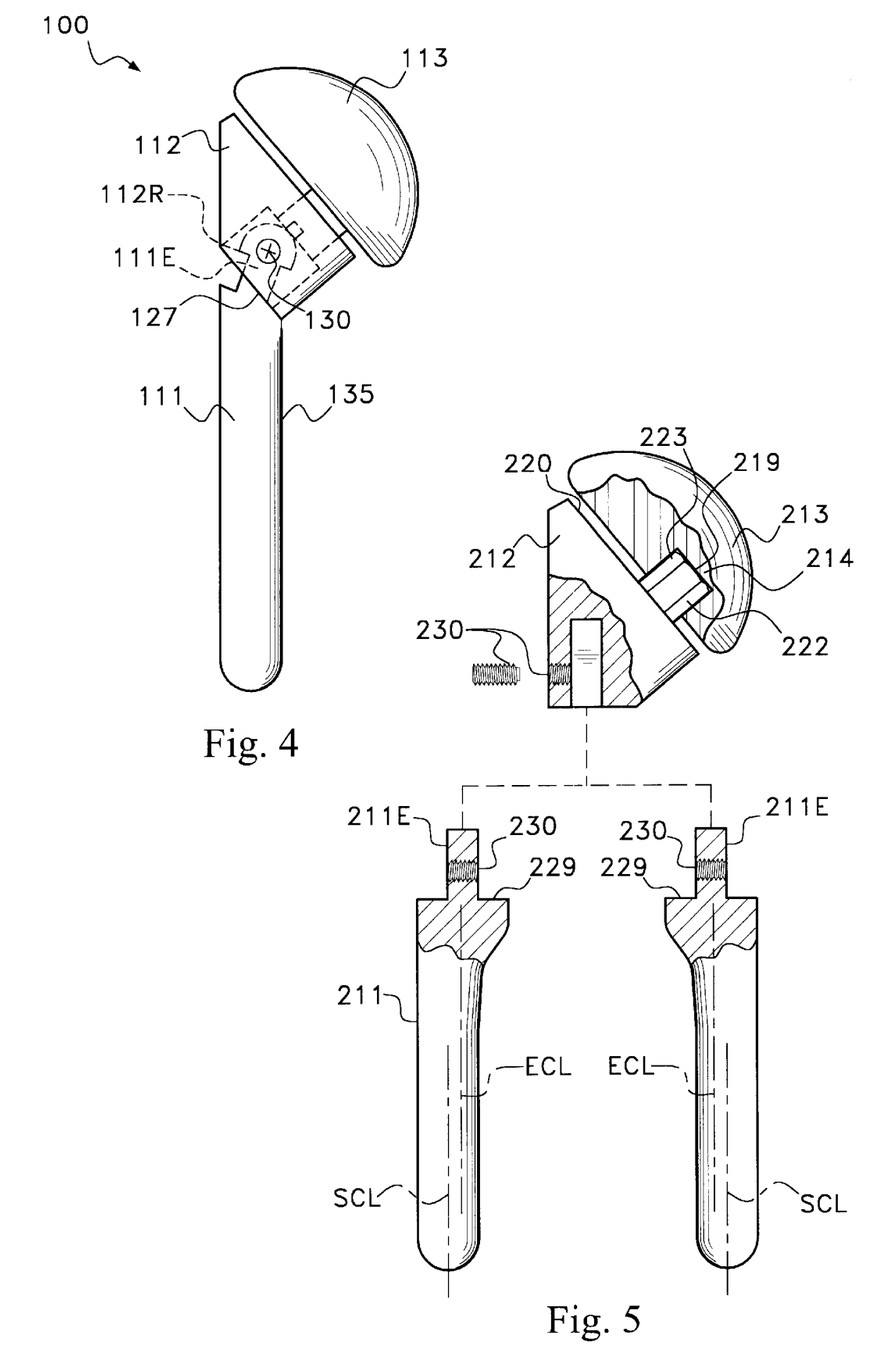
FIG. 4 is a side elevational view of a humeral prosthetic device according to a second exemplary embodiment of the present invention that provides an alternate method for achieving a plurality of selectable head-to-stem angles.
FIG. 5 is a partially exploded side elevational view a humeral prosthetic device according to a third exemplary embodiment of the present invention with the head, body, and stem shown in partial section.

FIG. 4 illustrates a humeral prosthetic device 100 according to a second exemplary embodiment of the present invention which provides an alternate method for achieving a plurality of selectable head-to-stem angles. The prosthetic device of this embodiment includes a stem 111 having an extension 111E extending from the superior end wall 129 into a recess 112R in body 112. The extension 111E permits medial-lateral rotation of the body 112 with respect to stem 111 about a fixed shaft 130, such rotation being limited by abutment of the base wall 127 of the body 112 with the side wall 135 of the stem 111. This construction permits the head-to-stem angle and lateral body offset to be adjusted approximately 20–30 degrees.

FIG. 5 illustrates a humeral prosthetic device 200 according to a third exemplary embodiment of the present invention. In this embodiment, the insert is replaced with a post 214 that extends from the inclined wall 220 of the body 212. The post 214 is unitary with the body 212 and couples the head 213 to the body 212. The peripheral surfaces 222, 223 of the post 250 and the corresponding recess 219 in the head 213 may be hexagonally shaped to provide six possible rotational positions of the head 413 relative to the body 212. Other body/recess peripheral surface arrangements, e.g., octagonal, cylindrical, splined surfaces, may be used to increase the precision of superior, inferior, anterior, and posterior positioning of the head 213.

The stem 211 in this embodiment is provided with a square coupling extension 211E that extends from the superior end wall 229 thereof. The coupling extension 211E has a center line ECL which is offset from the stem center line SCL. The stem 211 may be secured to the body 212 using any conventional fixation system, such as a simple set screw and screw aperture arrangement 230. The design of the stem 211 permits the body 212 to be offset relative to the stem by simply disassembly the stem 211 from the body 212, rotating the stem 211 180°, and then reassembling the stem 211 to the body 212. This in turn, permits the metaphyseal offset of the body 212 with respect to the canal of the humerus to be adjusted, thereby substantially eliminating the possibility of metaphyseal interference as is described below in connection with FIGS. 6A and 6B.

Figure 6A:
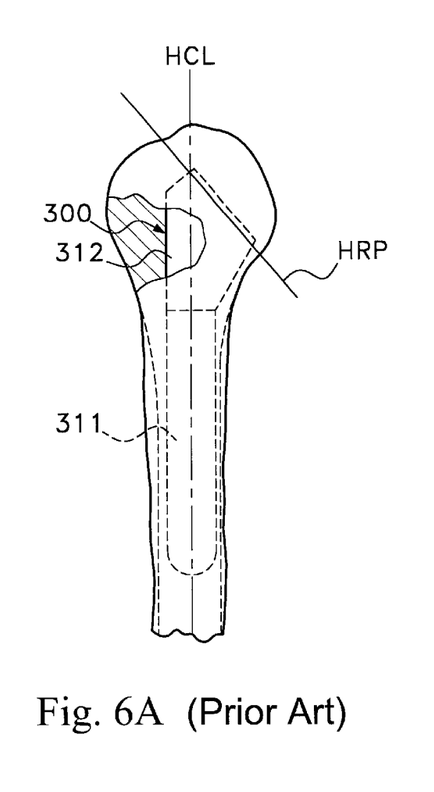

FIG. 6A illustrates a situation which can easily occur employing a conventional humeral prosthesis. The prosthesis, generally designated 300, includes a stem 311 and a body 312 shown in position in the humerus after installation. The anatomical head is shown, as well, as the humeral canal, the latter in dashed lines. The intended head resection plane HRP is also shown.

The humeral canal centerline HCL is shown, as well. Even though there is an acceptable fit of the stem 311 in the humeral canal, the body 312 exhibits interfacing contact with the humerus in the metaphyseal region which can prevent full seating of the prosthesis body and therefore the proper positioning of the prosthesis head (not shown).

Figure 6B:
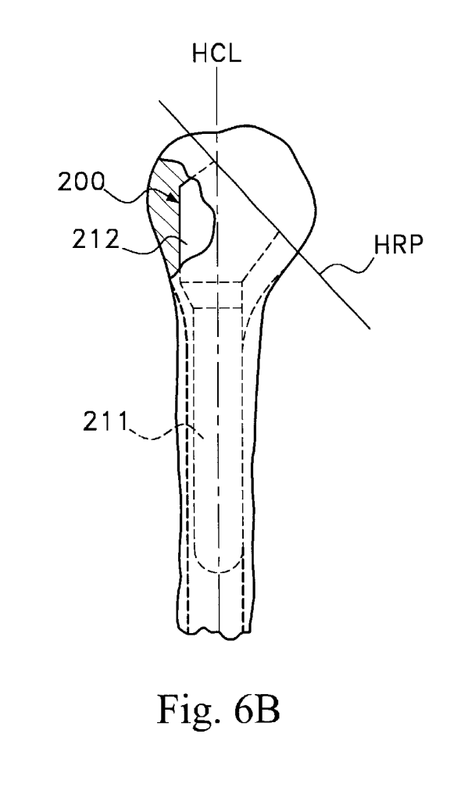

FIG. 6B illustrates how the humeral prosthetic device 200 of FIG. 5 provides a solution to the problem described above. As can be seen, the stem 211 of the device 200 has been reversed 180°, which provides lateral metaphyseal offset of the body 212, and head 213 (not shown) when in place. It should be noted that lateral metaphyseal offset of the body is also possible to achieve with the prosthetic devices of the previous embodiments.

FIGS. 7A–7D collectively illustrate a humeral prosthetic device 400 according to a fourth exemplary embodiment of the present invention. In this embodiment, the stem 411 includes a disc-shape coupling extension 411E which is connected to the superior end wall 429 of the stem 411 by a neck member 440. The body 412 includes a slot 412S which extends through the base wall 427 and opens into a spherical cavity 412C in the body 412. A locking set screw 430, extends into the cavity 412C where it engages the outer rim surface of the coupling extension 411E. The superior end wall 429 of the stem 411 or the base wall 427 of the body 412 may be orthogonal to the stem center line (SCL) or inclined for example, by 5 degrees. The stem 411 of this embodiment is reversible from the position shown in FIG. 7A to provide a lateral offset of the body 412 and the head 413. Each of the two configurations (not-reversed and reversed) in this example would therefore differ in inclination by approximately 10 degrees.

Figures 7A, 7B:
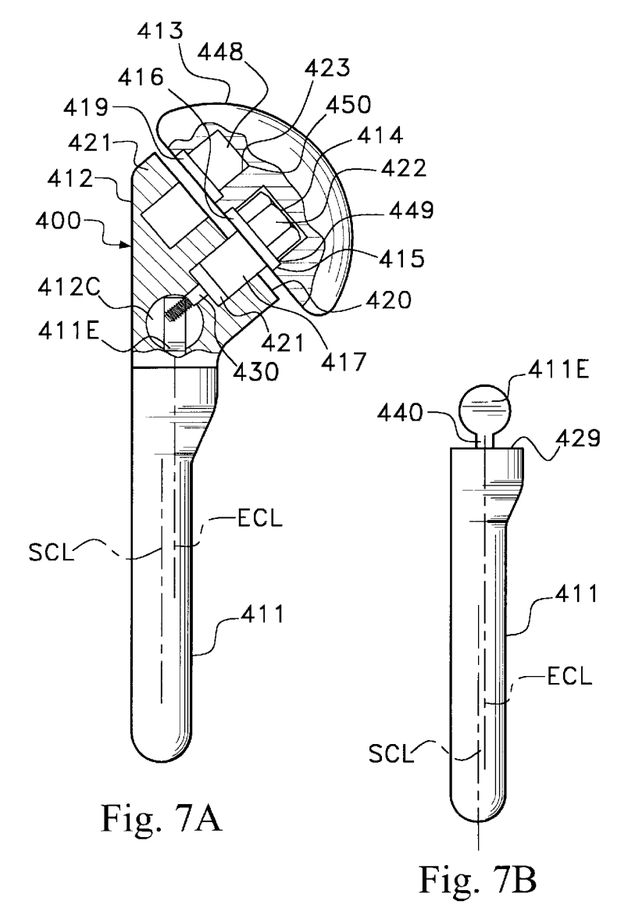
FIG. 7A is side elevational view of a humeral prosthetic device according to a fourth exemplary embodiment of the present invention with the body and head shown in partial section.
FIG. 7B is a side elevational view of the stem of the prosthetic device of FIG. 7A.
Figure 7C:
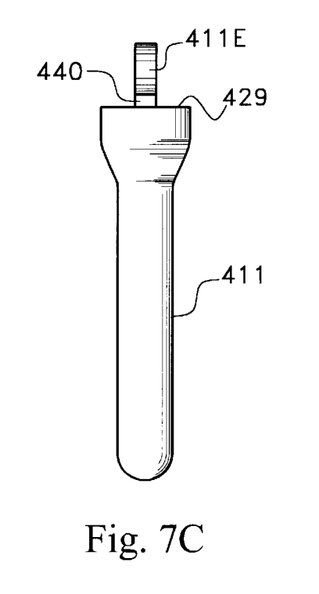
FIG. 7C is an elevational view of the stem of FIG. 7B rotated 90 degrees.
Figure 7D:
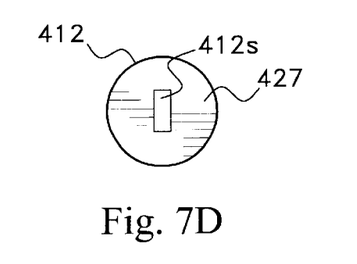
FIG. 7D is an bottom plan view of the body of FIG. 7A.

FIG. 7D shows the slot 412S in the base wall 427 of the body 412. Once the coupling extension 411E is inserted through the slot 412S, the stem 411 is rotated 90 degrees to a locking position, and thereafter locked in place by the set screw 430.

As shown in FIG. 7A, the insert 414 comprises a generally disc-shaped member 415 having a post 450 centrally disposed on a top surface 449 thereof and a locking projection 421 disposed on a lower surface 416 thereof in a central or offset position. The disc-shaped member 415 and the post 450 of the insert 414 may be nested in one or more stepped recesses 419 defined in the backside of the head 413.

Typically, the stepped recesses 419 are located at different offsets from the center line of the head, thereby enabling the surgeon to position the head 413 of the prosthesis with an even greater precision. The portion 448 of the stepped recess 419 that accommodates the post 450 may be tapered slightly for a press-fit lock with the post 450 of the insert 414. Alternatively, a set screw and screw aperture arrangement (not shown) or other conventional locking means may be employed to lock the insert 414 to the head 413. It The inclined wall 420 of the body 412 has one or more recesses 421 for receiving the locking projection 417 of the insert 414. The multiple recesses 421 defined in the inclined wall 420 of the body 412 provide even greater precision in positioning the head 413 of the prosthesis.

The peripheral surfaces 422, 423 of the post 450 and the portion 448 of the stepped recess 419 may be hexagonally shaped to provide six possible rotational positions of the insert 414 relative to the head 413. Other body/recess peripheral surface arrangements, e.g., octagonal, cylindrical, splined surfaces may be used to increase the precision of superior, inferior, anterior, and posterior positioning of the head 413 relative to the body 412/stem 411. Similarly, the peripheral surfaces 425, 426 of the locking projection 417 and the body recesses 421 may be square, cylindrical, splined, etc., to further increase the precision of superior, inferior, anterior, and posterior positioning of the head 413 relative to the body 412/stem 411.

Figure 8:
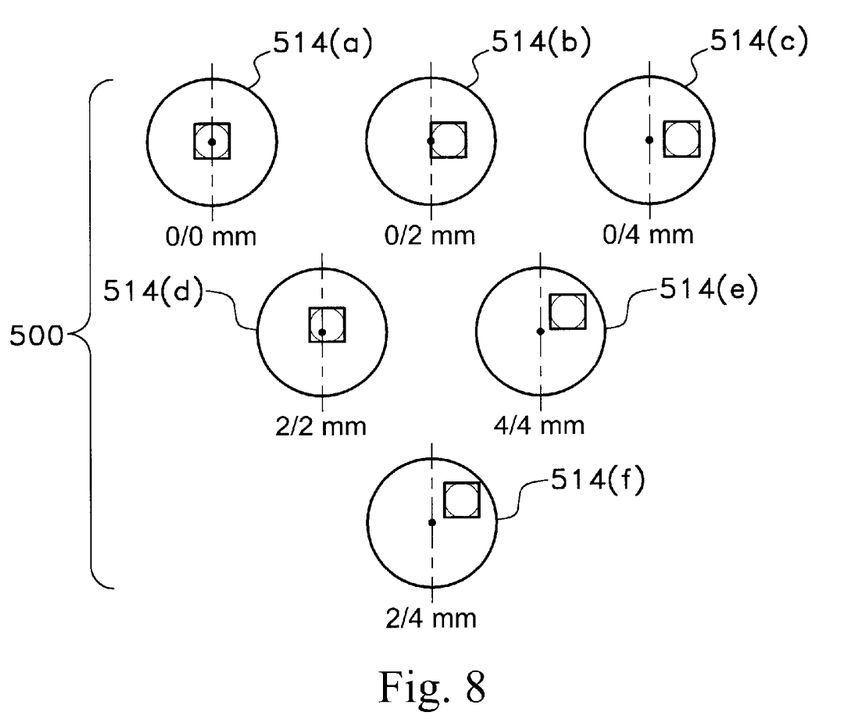
FIG. 8 is a bottom plan views of a series of inserts each having different offsets in two dimensions ranging from 0/0 millimeters to 4/4 millimeters.

All the inserts described herein can be provided as a series of inserts with locking projection offsets which vary, e.g., zero millimeters, two millimeters, four millimeters, etc. Providing a series of inserts reduces the inventory of heads. FIG. 8 illustrates the underside of a series 500 of inserts 514(a)–(f) similar to those previously described, which have locking projection offsets which vary in 2-millimeter increments as set forth below:

| INSERT | SUPERIOR | LATERAL |
| --- | --- | --- |
| 514 (a) 0/0 | none | none |
| 514 (b) 0/2 | zero millimeters | 2 millimeters |
| 514 (c) 0/4 | zero millimeters | 4 millimeters |
| 514 (d) 2/2 | 2 millimeters | 2 millimeters |
| 514 (e) 4/4 | 4 millimeters | 4 millimeters |
| 514 (f) 2/4 | 2 millimeters | 4 millimeters |

Each insert 514(a)–(f) has, for example, a square-shape locking projection 517, which permits rotation in 90° increments so that each of the inserts 514(b)–(f) can produce 4 different offsets for a total of 20 different incremental offsets plus the 0/0 offset of insert 514(a). Thus with a selection of 6 inserts 514(a)–(f), 21 different head offsets are possible within 1 millimeter of any desired location of the prosthesis head with respect to the humeral canal. Providing the inserts 514(a)–(f) with cylindrical-shape locking projections 517 substantially increases the number of head offset positions that may be achieved.

Figure 9:
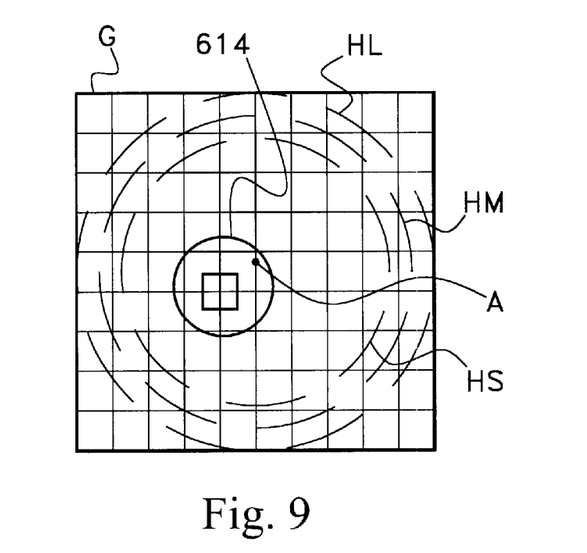
FIG. 9 is a plan view of a transparent lined grid for selecting an insert with the proper locking projection offset.

FIG. 9 illustrates a guide G according to an exemplary embodiment of the present invention. The guide aids the surgeon in selecting an insert from a series of inserts similar to that illustrated in FIG. 8. The guide G comprises a 2 millimeter spaced transparent grid which may be placed over the anatomical head severance plane with the residual head periphery concentric with the central axis A and with any of a number of concentric lines HL, HM, and HS which in this example respectively represent prosthetic heads of different radii here labeled head large, head medium, and head small. With the prosthetic body and stem in place, the appropriate prosthetic head radius may be determined. Similarly, the appropriate dimension of the insert in relation to the prosthesis body can be viewed through the guide G and the offset measured from A. In the shown example, the insert 614 appears with its center line at the approximate 225° or 7:30 position at a distance −2, −2 millimeters. In such case a 2/2 millimeter insert similar to insert (d) of FIG. 8 would be selected for optimum head positioning.

The Surgical Procedure

As will become apparent, the surgical procedure of the present invention serves to: 1) optimize the osteotomy and the orthopedic axis to accommodate central axis of canal, orientation of metaphyseal bone and near approximation of head position; 2) reproduce anatomy within realistic limits of surgical technique and minimize or overcome, the abnormalities of the joint due to degenerative joint diseases; 3) allows optimal metaphyseal fit and fill particularly for press fit prostheses, and; accommodates constraints in the canal and the metaphyseal region of the bone leading to a poor fit, distortion of the anatomy, or the necessity of using an undersized prosthesis.

Most prior techniques suggest reaming the canal after the osteotomy and determining the canal diameter by the "surgical feel" of the reamer when it engages cortical bone. Because of the flared shape of the proximal humerus, this technique arbitrarily defines a central axis of the canal as determined by the surgeon's general impression of where the center is and the distal point in the canal at which the reamer engages cortical bone. Two of the most recently introduced systems do suggest reaming the canal first and making an osteotomy of the head based on the reamed axis but with the intention of matching the anatomy to the prosthetic geometry rather than matching the prosthetic geometry to that of the native anatomy. As a result, the reamer assumed an even more arbitrary position because it was now constrained by the starting point in the humeral head in addition to the distal canal making reproduction of the anatomy even more challenging.

What is recommended in the present invention, is to view the central axis of the canal as a potential canal axis somewhat under the control of the surgeon in order to optimize its orientation to suit the prosthetic system. This should allow for shorter prostheses that more fully engage the proximal canal without further constraining the position of the prosthesis.

The procedure itself may require revisiting the chosen axis more than once in the preparation of the humerus.

First, the canal is reamed to a specified length through a generous opening in the top of the intact humeral head made after sufficient capsular releases to view the proximal humeral anatomy in two orthogonal planes, AP and lateral (the coronal and sagittal plane dimensions).

Depending on whether there is posterior offset of the humeral head, the view in the lateral dimension will suggest a compromise between the position of the head and the center of the canal. This compromised axis will also determine the plane of the humeral head resection.

In the medial-lateral dimension, one can expect some toggle in the reamer as the canal is more capacious in this plane. To the extent possible, the surgeon will choose a preferred axis orientation based on the inclination angles of the prosthetic systems available and the three dimensional anatomy of the patient. By surveying the orientation of the anatomic neck in relation to the available axes of the reamer, the surgeon makes decisions regarding the preferred axis of the canal and the intended plane of humeral head resection.

Appropriate jigs and attachments to the reamer may be constructed to help the surgeon with these decisions rather than relying completely on visual cues.

Broach/Insert Trial

The step of broaching and placing a trial insert prepares metaphyseal area for the prosthesis and allows a preliminary assessment of the position of the prosthesis.

Retroversion has already been determined by the humeral head osteotomy, so the broach must follow the line of the reamed canal. Since the body of the prosthesis has volume, this could represent a problem if there is significant offset between the plane of the resected head and the axis defined by the reamer. By necessity, the metaphyseal bone veers towards the canal center. If there is significant offset of the humeral head relative to the canal, the body of the prosthesis may hang up on the inner cortices in the metaphyseal region of the bone. In a more extreme case, the plane of humeral head resection may not only be offset from the canal center, but it could be tilted in such a way that directs the head even further away from the orientation of the metaphysis and stem altogether. In other words, the plane of the head resection may inadvertently exaggerate the head offset. Realizing that both of these parameters (canal center and plane of head resection) are somewhat arbitrary and both somewhat under the surgeon's control makes their more deliberate definition appealing.

In the procedure of the present invention, the broach also follows the reamed canal but the definition of this axis has been defined deliberately with an attempt at optimizing the fit of the prosthesis to the anatomy both in terms of the position of the prosthetic head and the fit in the metaphyseal bone. Accordingly, the variably shaped prosthetic bodies with variable relationships to the stem as described above are available that will require excavating the bone in different ways. For example, with existing prosthetic systems the bulk of the metaphyseal bone to be broached is always medial to the axis of the stem (the prior position of the reamer). This will not always be the case here where the body of the prosthesis may be laterally offset with respect to the central axis of the stem. Furthermore, the shape of the impression made into the metaphyseal bone will differ depending on the inclination of the original anatomy and chosen prosthetic.

In accordance with the prior art procedure, once the proximal humerus has been broached, the actual prosthesis is then impacted into the bone. This requires selection of the appropriate components from available inventory and their assembly into the correct geometric configuration in the operating room. Depending on manufacturing considerations, this may be the assembly of four distinct pieces—stem, body, insert, and head as disclosed above, or, for example, a wide array of single piece stem-body units may be one piece, requiring the assembly of only two pieces.

While the foregoing invention has been described with reference to the above embodiments, various modifications and changes can be made without departing from the spirit of the invention. Accordingly, all such modifications and changes are considered to be within the scope of the appended claims.

What is claimed is:

1. A humeral prosthetic device comprising:
   a body;
   a stem for anchoring the device in a humeral canal of a humerus, the stem coupled to a first area of the body; and
   a head for replacing a natural humeral head of the humerus, the head coupled to a second area of the body and disposed at a selected angle relative to the stem;
   at least one of the body and stem controlling the selected angle of the head relative to the stem;
   the body being disposed at a selected offset relative to the stem, at least one of the body and stem controlling the selected offset of the body relative to the stem, and the first area of the body defining a base wall disposed at one of a plurality of predetermined angles relative to a rear wall of the body, the predetermined angle of the base wall relative to the rear wall controlling the selected angle of the head relative to the stem and the selected offset of the body relative to the stem;
   wherein the body comprises a series of the bodies, each of the bodies having a different predetermined base wall to rear wall angle, the bodies being selectable for providing a desired selected angle of the head relative to the stem and a desired selected offset of the body relative to the stem.

2. A humeral prosthetic device comprising:
   a body having a base wall;
   a stem for anchoring the device in a humeral canal of a humerus, the stem having
   an end wall coupled to the base wall of the body; and
   a head for replacing a natural humeral head of the humerus, the head coupled to another wall of the body and disposed at a selected angle relative to the stem;
   at least one of the body and stem controlling the selected angle of the head relative to the stem;
   wherein the body is disposed at a selected offset relative to the stem, at least one of the body and stem controlling the selected offset of the body relative to the stem, and the stem includes a center line, the end wall disposed at one of a plurality of predetermined angles with respect to the center line, the predetermined angle of the end wall relative to the center line controlling the selected angle of the head relative to the stem and the selected offset of the body relative to the stem.

3. The humeral prosthetic device according to claim 2, wherein the stem comprises a series of the stems, each of the stems having a different predetermined end wall to center line angle, the stems being selectable for providing a desired selected angle of the head relative to the stem and a desired selected lateral offset of the body relative to the stem.

4. The humeral prosthetic device according to claim 2, wherein the stem includes an end wall and a center line, the end wall disposed at one of a plurality of predetermined angles with respect to the center line, the predetermined angle of the end wall relative to the center line controlling the selected angle of the head relative to the stem.

5. The humeral prosthetic device according to claim 2, further comprising an insert which coacts with the body and the head to provide superior, inferior, anterior, and posterior positioning of the head relative to the body.

6. The humeral prosthetic device according to claim 5, wherein the insert includes a locking projection laterally offset from a central axis of the insert.

7. The humeral prosthetic device according to claim 6, wherein the another wall of the body comprises an inclined wall which defines at least one aperture for receiving the locking projection of the insert.

8. The humeral prosthetic device according to claim 7, wherein the locking projection and the at least one aperture include peripheral surfaces which enable the insert to be rotatively positioned relative to the body in a selective manner.

9. The humeral prosthetic device according to claim 5, wherein the head includes a back side that defines at least one recess for receiving the insert, the at least one recess being laterally offset from a central axis of the head.

10. The humeral prosthetic device according to claim 9, wherein the insert and the at least one recess include peripheral surfaces which are configured to enable the insert to be rotatively positioned relative to the head in a selective manner.

11. The humeral prosthetic device according to claim 5, wherein the insert includes a locking projection laterally offset from a central axis of the insert and the head includes a back side that defines at least one recess for receiving the insert, the at least one recess being laterally offset from a central axis of the head.

12. The humeral prosthetic device according to claim 11, wherein the another wall of the body comprises an inclined wall which defines at least one aperture for receiving the locking projection of the insert.

13. The humeral prosthetic device according to claim 12, wherein the locking projection and the at least one aperture include peripheral surfaces which enable the insert to be rotatively positioned relative to the body in a selective manner.

14. The humeral prosthetic device according to claim 12, wherein the insert and the at least one recess include peripheral surfaces which are configured to enable the insert to be rotatively positioned relative to the head in a selective manner.

15. The humeral prosthetic device according to claim 12, wherein the locking projection and the at least one aperture include peripheral surfaces which enable the insert to be rotatively positioned relative to the body in a selective manner and the insert and the at least one recess include peripheral surfaces which are configured to enable the insert to be rotatively positioned relative to the head in a selective manner.

16. The humeral prosthetic device according to claim 2, further comprising a post which coacts with the head to provide superior, inferior, anterior, and posterior positioning of the head relative to the body.

17. The humeral prosthetic device according to claim 16, wherein the head includes a back side which defines at least one recess for receiving the post, the at least one recess being laterally offset from a central axis of the head.

18. The humeral prosthetic device according to claim 17, wherein the post and the at least one recess include peripheral surfaces which are configured to enable the head to be rotatively positioned relative to the body in a selective manner.

19. A humeral prosthetic device comprising:

a body;

a stem for anchoring the device in a humeral canal of a humerus, the stem coupled to a first area of the body; and a head for replacing a natural humeral head of the humerus, the head coupled to a second area of the body and disposed at a selected angle relative to the stem;

at least one of the body and stem controlling the selected angle of the head relative to the stem;

the first area of the body defining a base wall disposed at one of a plurality of predetermined angles relative to a rear wall of the body, the predetermined angle of the base wall relative to the rear wall controlling the selected angle of the head relative to the stem;

wherein the body comprises a series of the bodies, each of the bodies having a different predetermined base wall to rear wall angle, the bodies being selectable for providing a desired selected angle of the head relative to the stem.

20. A humeral prosthetic device comprising:

a body;

a stem for anchoring the device in a humeral canal of a humerus, the stem coupled to a first area of the body; and a head for replacing a natural humeral head of the humerus, the head coupled to a second area of the body and disposed at a selected angle relative to the stem;

at least one of the body and stem controlling the selected angle of the head relative to the stem;

the stem including an end wall and a center line, the end wall disposed at one of a plurality of predetermined angles with respect to the center line, the predetermined angle of the end wall relative to the center line controlling the selected angle of the head relative to the stem;

wherein the stem comprises a series of the stems, each of the stems having a different predetermined end wall to center line angle, the stems being selectable for providing a desired selected angle of the head relative to the stem.

* * * * *